United States Patent [19]

Harada et al.

[11] 4,273,933
[45] Jun. 16, 1981

[54] MODIFIED CATALYST FOR STEREO-DIFFERENTIATING REDUCTION OF CARBONYL COMPOUNDS AND PROCESS FOR REDUCTION WITH SAME CATALYST

[75] Inventors: Tadao Harada, Takarazuka; Yoshiharu Izumi, Kobe; Shinichiro Komatsu, Kawagoe, all of Japan

[73] Assignee: Kawaken Fine Chemicals Co., Ltd., Tokyo, Japan

[21] Appl. No.: 33,150

[22] Filed: Apr. 25, 1979

[51] Int. Cl.³ .................. C07C 69/675; C07C 31/26; C07C 31/20; C07C 33/26
[52] U.S. Cl. .................. 560/179; 568/807; 568/814; 568/830; 568/862; 568/863; 568/881
[58] Field of Search .............. 560/179; 568/807, 862, 568/863, 814, 830, 881

[56] References Cited

FOREIGN PATENT DOCUMENTS 39-22943 10/1964 Japan .

OTHER PUBLICATIONS

Izumi, "Angew. Chem. Intern. Ed." vol. 10, No. 12 (1971) pp. 871–881.
Orito et al., "Journal of Organic Synthetic Chemical Society" (Japan) 34, 236–239 (1976).
Orito et al., "Journal of Organic Synthetic Chemical Society" (Japan) 34, 672–674 (1976).
Orito et al., "Journal of Organic Synthetic Chemical Society" (Japan) 35, 753–754 (1977).

*Primary Examiner*—Joseph E. Evans
*Attorney, Agent, or Firm*—McAulay, Fields, Fisher, Goldstein & Nissen

[57] ABSTRACT

A modified nickel catalyst used for stereo-differentiating reduction of carbonyl compounds is provided. The modified nickel catalyst is prepared by soaking a nickel catalyst in an aqueous modifying medium having dissolved therein at least one inorganic salt, such as sodium bromide or sodium chloride, and at least one optically active substance, such as optically active hydroxy acid. The modified nickel catalyst exhibits enhanced activity for stereo-differentiating reduction and causes little or no side reactions, and thus, brings about an extremely high yield of the reaction product.

4 Claims, No Drawings

MODIFIED CATALYST FOR STEREO-DIFFERENTIATING REDUCTION OF CARBONYL COMPOUNDS AND PROCESS FOR REDUCTION WITH SAME CATALYST

BACKGROUND OF THE INVENTION

1. Field of the Invention

This invention relates to a modified catalyst for stereo-differentiating reduction of carbonyl compounds and a process for stereo-differentiating reduction with the same catalyst.

By the term "stereo-differentiating reduction" is meant stereo chemical reduction by which one of a pair of enantiomers, each having at least one asymmetric carbon atom, is produced selectively, i.e., in an amount larger than that of the other enantiomer. The stereo-differentiating reduction is classified into enantioface- and diastereo-differentiating reductions, by which optical isomers having one asymmetric carbon atom and those having two asymmetric carbon atoms are produced, respectively. The present invention may be said to pertain to stereo-differentiating hydrogenation of carbonyl compounds with a modified catalyst.

2. Description of the Prior Art

One of the coinventors, Mr. Izumi, first proposed stereo-differentiating reduction of amino acids with a heterogeneous catalyst comprising silk and palladium in 1956 and, further, with a heterogeneous Raney nickel catalyst modified with optically active tartaric acid. The inventors have proposed the stereo-differentiating reduction with a heterogeneous modified catalyst in Japanese Patent Publication No. 22,943/1964 and Angew. Chem. Intern. Ed. Engl., 10, 871 (1971). It is taught in these references that acetoacetic acid esters can be reduced with an stereo-differentiating modified catalyst into 3-hydroxybutyric acid esters at a high optical yield. Furthermore, the inventors achieved an extremely high optical yield of 85% at highest, in 1977, in stereo-differentiating reduction of methyl acetoacetate with a modified nickel catalyst.

Some other research on various stereo-differentiating reduction catalysts has been conducted which catalysts originate in the inventor's stereo-differentiating reduction catalysts. For example, Orito et al: Journal of Organic Synthetic Chemical Society (Japan) 34, 236 (1976), ibid. 34, 672 (1976) and ibid. 35, 753 (1977), reported that nickel-platinum group metal-diatomaceous earth catalysts modified with tartaric acid were active for stereo-differentiating reduction, and particularly those which contain palladium as the platinum group metal brought about an optical yield of approximately 90%. These catalysts are, however, not advantageous in the following points. First, the catalysts necessitate special carriers and it is difficult to prepare the catalysts. This fact materially affects the reproducibility of the optical yield. Secondly, a platinum group metal is expensive. Thirdly, the catalysts inevitably cause side reactions which lead to reduction in the chemical yield of the product.

SUMMARY OF THE INVENTION

A main object of the present invention is to provide an improved modified catalyst for stereo-differentiating reduction which catalyst is convenient to prepare, not expensive and characterized as exhibiting enhanced activity for stereo-differentiating reduction, and causing little or no side reactions, and thus, brings about an extremely high yield of the product and a reliable reproducibility in the yield of the product.

Another object of the present invention is to provide a process for stereo-differentially reducing a carbonyl compound with the above-mentioned modified catalyst.

Other objects and advantages of the present invention will be apparent from the following description.

In one aspect of the present invention, there is provided a modified catalyst used for enantioface-differentiating reduction of carbonyl compounds, characterized by being prepared by soaking a nickel catalyst in an aqueous modifying medium having dissolved therein at least one inorganic salt and at least one optically active substance.

In another aspect of the present invention, there is provided a process for stereo-differentially reducing a carbonyl compound, characterized by being conducted in the presence of a modified catalyst prepared by soaking a nickel catalyst in an aqueous modifying medium having dissolved therein at least one inorganic salt and at least one optically active substance.

DESCRIPTION OF THE PREFERRED EMBODIMENTS

The catalyst of the invention is characterized as being modified not by an optically active substance alone, but by a combination of an optically active substance with an inorganic salt. Due to such combination, the catalyst of the invention exhibits extremely enhanced stereo-differentiating ability, causes little or no side reactions and brings about a reliable reproducibility in the yield of the product. For example, as substantiated in the working examples below, methyl 3-hydroxybutyrate can be obtained from methyl acetoacetate at an optical yield of 92.1% and, more surprisingly, (R.R)2,4-pentanediol can be obtained at an optical yield of 100%.

The optically active substance used for the preparation of the modified catalyst of the invention is not particularly limited. However, hydroxycarboxylic acids are preferable, such as, for example, optically active tartaric acid, optically active lactic acid and optically active malic acid. Of these, optically active tartaric acid is optimum. Optically active amino acids may also be used, which include, for example, valine, leucin and glutamic acid. These optically active substances may be used alone or in combination.

The inorganic salt used is also not particularly limited. Water-soluble neutral salts are preferable, which include, for example, halides, sulfates and nitrates of alkali metals, alkaline earth metals and iron group metals. Of these, alkali halides, such as sodium bromide and sodium chloride, are particularly preferable. Sodium sulfate and nickel bromide are preferable. These inorganic acids may be used alone or in combination.

The nickel catalyst to be modified may be selected from any known nickel catalysts, such as Raney nickel catalyst, decomposing nickel formate catalyst and reducing nickel catalyst. Of these, Raney nickel catalyst is particularly preferable. The nickel catalyst may be supported on a conventional carrier, such as diatomaceous earth or alumina.

The modified catalyst of the invention is prepared by soaking the nickel catalyst in an aqueous modifying medium having dissolved therein the above-mentioned inorganic salt and optically active substance. The amounts of the inorganic salt and the optically active substance dissolved in the aqueous modifying medium are not particularly limited, and may preferably be in the ranges of from 0.006 to 25 times, by weight, and from 0.3 to 3 times, by weight respectively, of the amount of metallic nickel in the nickel catalyst.

The pH of the aqueous modifying medium may suitably be adjusted so as to be at least 2.0, depending upon the particular carbonyl compound to be reduced. The pH is more preferably in the range of from 2 to 8. The temperature of the aqueous modifying medium is not particularly limited. However, the aqueous modifying medium is preferably maintained at a temperature of 0° to 150° C., more preferably 80° to the boiling point thereof. The soaking treatment may conveniently be carried out at normal pressures, although the treatment may be carried out at super-atmospheric pressures. The soaking period of time is also not particularly limited. For example, the soaking treatment is carried out over a period of one to three hours, preferably while the medium is stirred. If desired, the soaking may be repeated.

Depending upon the particular carbonyl compound to be reduced and the particular solvent used upon the reduction of the carbonyl compound, the modified nickel catalyst as withdrawn from the aqueous modifying medium may be either directly used for the stereo-differentiating reduction, or washed with water or a suitable solvent, such as methanol, prior to the use for the stereo-differentiating reduction.

The carbonyl compound to be reduced with the catalyst of the invention is a compound having at least one carbonyl group which is capable of being hydrogenated thereby, to be converted to a hydroxyl group bonded to an asymmetric carbon atom of a secondary alcohol. Such a carbonyl compound includes, for example, those which are represented by the general formulae (I), (II), (III) and (IV):

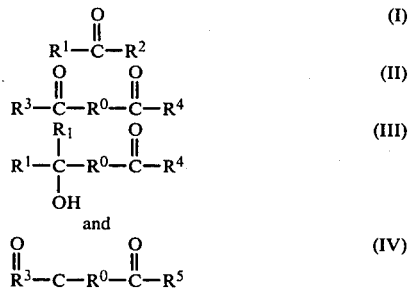

wherein each of $R^1$, $R^2$, $R^3$ and $R^4$ is a substituted or unsubstituted alkyl group having 1 to 12 carbon atoms, a substituted or unsubstituted aryl group having 6 to 14 carbon atoms, a substituted or unsubstituted aralkyl group having 7 to 15 carbon atoms or a substituted or unsubstituted alkylaryl group having 7 to 17 carbon atoms, $R^1$ and $R^2$ are different from each other and may form together a ring, and $R^3$ and $R^4$ may be identical to or different from each other and may form together a ring; and, $R^5$ is a hydroxyl group or a substituted or unsubstituted alkoxy group having 1 to 12 carbon atoms, and; $R^0$ is a straight-chain or branched alkylene group having 1 to 6 carbon atoms or a straight-chain alkylene group having a hydroxyl group or groups and having 1 to 6 carbon atoms. Of the carbonyl compounds, represented by the general formulae (I), (II), (III) and (IV), preferable are those which $R^1$, $R^2$, $R^3$ and $R^4$ are alkyl groups such as methyl, ethyl, propyl, butyl and octyl, and $R^0$ is an alkylene group, such as methylene, ethylene, propylene, isobutylene or tetramethylene. The values $R^1$, $R^2$, $R^3$, $R^4$ and $R^5$ may have a substituent such as a halogen atom, a hydroxyl group, an alkoxy group or a carboxylate group.

The carbonyl compounds represented by the general formulae (I), (II), (III) and (IV) include, for example, keto-acid esters, such as methyl acetoacetate and ethyl acetoacetate; diketones, such as acetylacetone and dibenzoylmethane; hydroxy-ketones, such as diacetone alcohol, acetone alcohol and ketose, and; acetophenone, 2-hexanone and menthone.

The optically active secondary alcohol produced by the stereo-differentiating reduction process of the invention includes, for example, compounds which are represented by the general formulae (V), (VI), (VII) and (VIII):

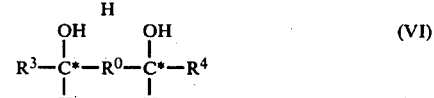

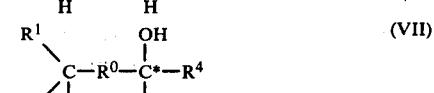

and

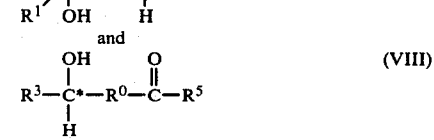

wherein the asterisked carbon refers to an asymmetric center, and $R^0$, $R^1$, $R^2$, $R^3$, $R^4$ and $R^5$ are the same as defined above. The secondary alcohols represented by the general formulae (V), (VI), (VII) and (VIII) are, for example, methyl 3-hydroxybutyrate, ethyl 3-hydroxybutyrate, 2,4-pentanediol, 1,3-diphenyl-1,3-propanediol, 2-methyl-2,4-pentanediol, mannitol, sorbitol, phenethyl alcohol, 2-hexanol and menthol.

The stereo-differentiating reduction of carbonyl compounds may be carried out in a solvent or without the use of a solvent and in the presence of the modified nickel catalyst of the invention. The reduction procedure may be conventional per se. It is, however, preferable, in order to attain a more enhanced optical yield of the intended secondary alcohol, that a solvent and an acid additive be used. The solvent used includes, for example, esters, such as methyl propionate and methyl acetate, and cyclic ethers, such as tetrahydrofuran and dioxane. Water and alcohols may also be used depending upon the particular carbonyl compound to be reduced. The acid additive used includes, for example, an organic acid, such as acetic acid, and an inorganic acid, such as hydrochloric acid. Incorporation of a minor amount of such acid additives makes the hydrogenation proceed smoothly and stably.

The Raney nickel catalyst prepared by alkali treatment of the alloy may preferably be treated, prior to the use for stereo-differentiating hydrogenation, with an aqueous glycolic acid, the pH of which has been adjusted by adding thereto sodium hydroxide, for performing the hydrogenation smoothly and stably.

The stereo-differentiating hydrogenation may be carried out at an atmospheric pressure or a superatmospheric pressure less than 150 kg/cm$^2$. However, the reaction pressure is practically preferably in the range of from 50 to 150 kg/cm$^2$ from the standpoint of the rate of reaction.

When the reaction is completed, the catalyst is filtered off from the reaction mixture and the solvent is separated from the filtrate in a conventional manner, whereby the intended secondary alcohol is obtained.

The reason for the extreme enhancement of the stereo-differentiating ability of the catalyst of the invention cannot be elucidated, but is presumed to be as follows. An optically active substance is adsorbed on a predominant part of the active sites present on the nickel catalyst during the step of modifying the nickel catalyst, which part thereby exhibits stereo-differentiating ability. A carbonyl compound, upon having access to the active sites having adsorbed thereon the active substance is stereo-differentially hydrogenated. If the nickel catalyst is modified with the optically active substance alone, the remaining part of the active sites, which part has not adsorbed thereon the optically active substance, produce an alcohol of a racemic form. In contrast, when the nickel catalyst is modified with both an optically active substance and an inorganic salt, the inorganic salt makes inactive a part of the active sites, on which part the optically active substance is not adsorbed. Thus, the nickel catalyst modified with both the optically active substance and the inorganic salt produces the intended secondary alcohol with enhanced optical yield.

The invention will be further illustrated by the following examples, wherein percents are by weight unless otherwise specified.

EXAMPLE 1

Preparation of modified nickel catalyst 1.9 g of a well pulverized Raney nickel powder (Ni:Al=42:58) were incorporated in fine lots at room temperature into an aqueous solution of 4.5 g of sodium hydroxide in 20 ml of water. The mixture, so obtained, was heated to a temperature of 100° C. and maintained at that temperature for one hour. Then, the Raney nickel catalyst was separated from the aqueous alkaline solution, and then, washed 15 times with 30 ml portions of water.

1 g of Ds-(+)-tartaric acid and 5 g of sodium bromide were dissolved in 100 ml of water, and then, the pH of the aqueous solution was adjusted to 3.2 by adding sodium hydroxide thereto, thereby to form a modifying medium. 0.8 g of the above-mentioned Raney nickel catalyst was incorporated in the modifying medium. The suspension, so obtained, was heated to a temperature of 100° C. and, while being stirred at intervals, maintained at that temperature for one hour. Thereafter, the supernatant liquid was removed from the suspension, and the residue was washed once with 10 ml of water, twice with 50 ml of methanol and, finally once with 25 ml of methyl propionate. The modified Raney nickel catalyst, so prepared, contained 1.5% of tartaric acid and 0.64% of sodium bromide based on the weight of the modified Raney nickel catalyst.

Hydrogenation 0.8 of the above-mentioned Raney nickel catalyst, 23 ml of methyl propionate and 12.4 g of methyl acetoacetate were placed in a 100 ml volume autoclave. The autoclave was flashed with hydrogen and, when the pressure reached 90 kg/cm$^2$, the content was heated to a temperature of 100° C. and maintained at this temperature while being stirred. Fine hours after heating began no more hydrogen uptake was observed. Stirring of the content, however, continued for a further 20 minutes. The reaction product was taken out from the autoclave, and then, the catalyst was filtered off from the reaction product. The filtrate was distilled, thereby to obtain methyl 3-hydroxybutyrate. The methyl 3-hydroxybutyrate exhibited an optical rotation $[\alpha]_D^{16}$ of $-19.1$ (neat). The optical purity of the methyl 3-hydroxybutyrate was determined as 86.6% based on the value of $[\alpha]_D^{16} = -22.05$ (neat) for (R)-methyl 3-hydroxybutyrate.

EXAMPLE 2

Using a modified Raney nickel catalyst similar to that prepared in Example 1 and following a hydrogenation procedure similar to that employed in Example 1, methyl 3-hydroxybutyrate was prepared, wherein 0.2 ml of acetic acid was added to the starting reaction mixture, with all other conditions remaining substantially the same. The resultant methyl 3-hydroxybutyrate exhibited an optical rotation $[\alpha]_D^{16}$ of $-20.1$ (neat) and an optical purity of 91.2%.

EXAMPLE 3

Using a modified Raney nickel catalyst similar to that prepared in Example 1 and following a hydrogenation procedure similar to that employed in Example 1, methyl 3-hydroxybutyrate was prepared, wherein 0.2 mol of acetic acid was added to the starting reaction mixture and the initial pressure of hydrogen was changed to 50 kg/cm$^2$, with all other conditions remaining substantially the same. The methyl 3-hydroxybutyrate, obtained after the reaction for 5 hours, exhibited an optical rotation $[\alpha]_D^{16}$ of $-19.8$ (neat) and an optical purity of 89.8%.

EXAMPLE 4

Using a modified Raney nickel catalyst similar to that prepared in Example 1 and following a procedure similar to that employed in Example 1, methyl 3-hydroxybutyrate was prepared, wherein 0.2 ml of acetic acid was used and tetrahydrofuran was used as the reaction medium instead of methyl propionate, with all other conditions remaining substantially the same. The resultant methyl 3-hydroxybutyrate exhibited an optical rotation $[\alpha]_D^{16}$ of $-18.7\%$ (neat) and an optical purity of 84.8%.

EXAMPLE 5

The procedure employed in Example 4 was repeated, wherein ethyl acetate was used as the reaction medium instead of tetrahydrofuran, with all other conditions remaining substantially the same. The resultant methyl 3-hydroxybutyrate exhibited an optical rotation $[\alpha]_D^{16}$ of $-19.8$ (neat) and an optical purity of 89.8%.

EXAMPLE 6

The procedure for modifying the Raney nickel catalyst, employed in Example 1, was repeated, wherein Ls-(−)-tartaric acid was used in place of Ds-(+)-tartaric acid, with all other conditions remaining substantially the same. Using the modified Raney nickel catalyst so prepared, methyl 3-hydroxybutyrate was prepared in a manner similar to that employed in Example 2. The resultant (S)-methyl 3-hydroxybutyrate exhibited an optical rotation $[\alpha]_D^{16}$ of +18.72 (neat) and an optical purity of 84.9%.

EXAMPLES 7 AND 8

The Raney nickel catalyst, which was taken out from the modifying medium and, then, washed with water in the modification procedure mentioned in Example 1, was again soaked in a modifying medium similar to that used in Example 1, whereby a modified catalyst A was prepared. The modified catalyst A was soaked in a modifying medium similar to that used in Example 1, whereby a modified catalyst B was prepared. Using each of the modified catalysts A and B, methyl 3-hydroxybutyrate was prepared in a manner similar to that employed in Example 2. The resultant methyl 3-hydroxybutyrates exhibited optical purities of 89.5% and 92.1%, respectively.

COMPARATIVE EXAMPLE 1

A Raney nickel catalyst was modified in a manner similar to that employed in Example 1 except that sodium bromide was not incorporated in the modifying medium. Using the resultant modified Raney nickel catalyst, methyl acetoacetate was hydrogenated in a manner similar to that employed in Example 2. The resultant product exhibited an optical purity of 40.7%.

EXAMPLES 9 THROUGH 14

A Raney nickel catalyst was modified in a manner similar to that employed in Example 1 except that each of the inorganic salts listed in Table below, was incorporated in the modifying medium in place of sodium bromide. Using the resultant modified Raney nickel catalysts, methyl acetoacetate was hydrogenated in a manner similar to that employed in Example 2. The optical purities of the resultant products are shown in Table I, below.

TABLE I

| Example No. | Inorganic salt (amount in g) | Optical purity in % |
|---|---|---|
| 9 | NaF(3) | 60.8 |
| 10 | NaCl(10) | 74.9 |
| 11 | NaI(5 × 10$^{-4}$) | 53.2 |
| 12 | Na$_2$SO$_4$(10) | 58.6 |
| 13 | NaNO$_3$(0.1) | 55.1 |
| 14 | NiBr$_2$(1) | 65.0 |

EXAMPLE 15

The hydrogenation procedure employed in Example 2 was repeated, wherein ethyl acetoacetate was used as the carbonyl compound to be hydrogenated, instead of methyl acetoacetate, with all other conditions remaining substantially the same. The resultant ethyl 3-hydroxybutyrate exhibited an optical rotation $[\alpha]_D^{16}$ of −15.5 (neat) and an optical purity of 62%.

EXAMPLE 16

The procedure employed in Example 1 was repeated, wherein 1-butanol-3-one was used as the carbonyl compound to be hydrogenated, instead of methyl acetoacetate, and the pH of the modifying medium was adjusted to 4.0 instead of 3.2, with all other conditions remaining substantially the same. The resultant 1.3-butanediol exhibited an optical rotation $[\alpha]_D^{20}$ of −19.38(C.10EtOH) and an optical purity of 67%.

EXAMPLE 17

The procedure employed in Example 2 was repeated, wherein diacetone alcohol was used as the carbonyl compound to be hydrogenated, instead of methyl acetoacetate, and the pH of the modifying medium was adjusted to 4.0 instead of 3.2, with all other conditions remaining substantially the same. The resultant 2-methyl-2,4-pentanediol exhibited an optical rotation $[\alpha]_D^{20}$ of −12.88 (neat) and an optical purity of 78%.

EXAMPLE 18

Following a modification procedure similar to that employed in Example 1, a modified Raney nickel catalyst was prepared from 3.8 g of a Raney nickel alloy, 2 g of tartaric acid and 16 g of sodium bromide. Using this modified Raney nickel catalyst, the hydrogenation procedure employed in Example 2 was repeated, wherein 11.5 g of acetone alcohol were used as the carbonyl compound to be hydrogenated, instead of methyl acetoacetate, and the filtrate of the hydrogenated product was distilled at a temperature of 110° C. and a reduced pressure of 20 mmHg, with all other conditions remaining substantially the same. The resultant 2,4-pentanediol exhibited an optical rotation $[\alpha]_D^{20}$ of −10.73 (neat). The 2,4-pentanediol was proved by gas chromatography to be comprised of 35.5% of meso form and 64.5% of erythro form.

EXAMPLE 19

Following a modification procedure similar to that employed in Example 1, a modified Raney nickel catalyst was prepared from 2.5 g of a Raney nickel alloy, 2.5 g of Ds-(+)-tartaric acid and 10 g of sodium bromide. Using this modified Raney nickel catalyst, stereo-differentiating hydrogenation was carried out under the following conditions.

| | |
|---|---|
| Carbonyl Compound: | 25 g of D-(−)-fructose |
| Reaction medium: | water |
| Initial pressure of hydrogen: | 100 kg/cm$^2$ |
| Reaction temperature: | 125° C. |
| Reaction time: | 4 hours |

After the catalyst was filtered off from the reaction product, the reaction product was analyzed by gas chromatography. The product was comprised of 55% of mannitol and 45% of sorbitol.

For comparison purposes, the above-mentioned hydrogenation procedure was repeated, wherein the unmodified Raney nickel catalyst was used instead of the modified one with all other conditions remaining substantially the same. The resultant product was comprised of 50% of mannitol and 50% of sorbitol.

EXAMPLE 20

Following a modification procedure similar to that employed in Example 1, a modified Raney nickel catalyst was prepared from 38 g of a Raney nickel alloy, 20 g of Ds-(+)-tartaric acid and 160 g of sodium bromide. This modified Raney nickel catalyst was placed together with 100 g of acetylacetone and 200 ml of tetrahydrofuran in one liter volume autoclave. The stereo-differentiating hydrogenation was carried out at an initial hydrogen pressure of 100 kg/cm$^2$ and a temperature of 100±5° C. for 7 hours. The catalyst was filtered off from the reaction product and the solvent was distilled off from the filtrate. 100 ml of ether were added to the so obtained residue, and the resultant solution was left to stand at a temperature of −50° C. over a period of three days, thereby to precipitate a crystal. The crystal was fractionated and, then, dissolved in 100 ml of ether. The resultant solution was allowed to stand overnight at a temperature of −5° C. After the crystal was filtered off from the solution, the crystal was distilled at a temperature of 110° C. and a reduced pressure of 20 mmHg. The distillate exhibited an optical rotation $[\alpha]_D^{20}$ of −54(C10, EtOH) and, thus, was identified as 2R, 4R-2,4-pentanediol. The yield was 67% and the optical purity was approximately 100%.

EXAMPLE 21

The procedure employed in Example 20 was repeated, wherein ethanol was used as the reaction medium instead of tetrahydrofuran, with all other conditions remaining substantially the same. The yield of 2R,4R-2,4-pentanediol was 70% and the optical purity thereof was approximately 100%.

EXAMPLE 22

Following a modification procedure similar to that employed in Example 1, a modified Raney nickel catalyst was prepared from 3.8 of a Raney nickel alloy, 2 g of Ds-(+)-tartaric acid and 16 g of sodium bromide. This modified Raney nickel catalyst was placed together with 10 g of dibenzoylmethane, 0.4 ml of acetic acid and 20 ml of tetrahydrofuran in a 200 ml volume. The stereo-differentiating hydrogenation was carried out at an initial hydrogen pressure of 100 kg/cm² and a temperature of 100° C. for 8 hours. The catalyst was filtered off from the reaction product and the solvent was distilled from the filtrate. 5 ml of ether were added to the so obtained residue, and the resultant solution was felt to stand overnight at a temperature of −50° C. After the supernatant liquid was removed therefrom, the precipitate was recrystallized at a temperature of −5° C. from 10 ml of ethyl acetate. The obtained crystal was further recrystallized twice in a similar manner and, finally, dried in a desiccator. The crystal was identified by NMR as 1R,3R-1,3-diphenyl-1,3-propanediol. The yield was 20% and the optical purity was 99%.

EXAMPLE 23

Following a procedure similar to that employed in Example 1, a Raney nickel catalyst was prepared from 1.8 g a Raney nickel alloy. After the Raney nickel catalyst was washed with water, the catalyst was incorporated in 100 ml of an aqueous 1% glycolic acid solution, the pH of which was previously adjusted to 3.2 by adding sodium hydroxide thereto. The mixture was maintained at a temperature of 100° C. for one hour. The catalyst was separated from the aqueous solution and, then, washed with water. Thereafter, the catalyst was incorporated in 100 ml of a modifying medium, which was prepared by incorporating 1 g of Ds-(+)-tartaric acid and 8 g of sodium bromide in water, and then, adjusting the pH of the aqueous solution to 5.0. The suspension, so obtained, was maintained in a ice-water bath for one hour while the suspension was stirred at intervals. Therefore, the supernatant liquid was removed from the suspension and the residue was washed once with 10 ml of water, twice with 50 ml of methanol, and finally, once with 25 ml of methyl propionate, thereby to obtain a modified Raney nickel catalyst.

Using the modified Raney nickel catalyst, the hydrogenation procedure employed in Example 1 was repeated, wherein hydrogenation was carried out for a period of 6 hours, with all other conditions remaining substantially the same. The resultant methyl 3-hydroxybutyrate exhibited an optical purity of 84.1%.

What we claim is:

1. A process for stereo-differentially reducing a carbonyl compound, wherein the carbonyl compound is contacted with a modified nickel catalyst prepared by soaking a nickel catalyst in an aqueous modifying medium having dissolved therein at least one optically active substance selected from the group consisting of optically active hydroxycarboxylic acids and optically active amino acids, and, then, separating the so-treated catalyst from the aqueous modifying medium, characterized in that the aqueous modifying medium has dissolved therein, in addition to the optically active substance, at least one inorganic salt said inorganic salt being contained in the modifying medium in an amount of from 0.006 to 25 times, by weight, based on the amount of metallic nickel in said nickel catalyst.

2. A process according to claim 1, wherein the stereo-differentiating reduction of a carbonyl compound is effected at a temperature of from 50° to 120° C.

3. A process according to claim 1, wherein the stereo-differentiating reduction of a carbonyl compound is effected at an atmospheric pressure or a superatmospheric pressure of not higher than 150 kg/cm².

4. A process according to claim 1, wherein the carbonyl compound is selected from the compounds represented by the general formulae (I), (II), (III) and (IV):

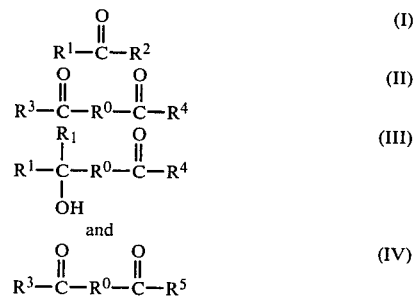

wherein each of $R^1$, $R^2$, $R^3$ and $R^4$ is a substituted or unsubstituted alkyl group having 1 to 12 carbon atoms, a substituted or unsubstituted aryl group having 6 to 14 carbon atoms, a substituted or unsubstituted aralkyl group having 7 to 15 carbon atoms or a substituted or unsubstituted alkylaryl group having 7 to 17 carbon atoms, $R^1$ and $R^2$ are different from each other and may form together a ring, and $R^3$ and $R^4$ may be identical to or different from each other and may form together a ring; $R^5$ is a hydroxyl group or a substituted or unsubstituted alkoxy group having 1 to 12 carbon atoms, and; $R^0$ is a straight-chain or branched alkylene group having 1 to 6 carbon atoms or a straight-chain alkylene group having a hydroxyl group or groups and having 1 to 6 carbon atoms.

* * * * *

UNITED STATES PATENT AND TRADEMARK OFFICE
CERTIFICATE OF CORRECTION

PATENT NO. : 4,273,933
DATED : June 16, 1981
INVENTOR(S) : Tadao Harada et al

It is certified that error appears in the above—identified patent and that said Letters Patent is hereby corrected as shown below:

Column 1, line 36    change "an" to --a--

Column 5, line 64    after "0.8" insert --g--

Column 6, line 2     change "Fine" to --Five--

Column 7, line 66    change "1.3" to --1,3--

Column 9, line 37    change "felt" to --left--

Signed and Sealed this

Fifth Day of January 1982

[SEAL]

Attest:

Attesting Officer

GERALD J. MOSSINGHOFF

Commissioner of Patents and Trademarks